United States Patent
Shipp (10) Patent No.: US 8,466,659 B2
(45) Date of Patent: Jun. 18, 2013

(54) DEVICE AND METHOD FOR RENDERING A BATTERY SAFE FOR DISPOSAL

(75) Inventor: John I. Shipp, Tullahoma, TN (US)

(73) Assignee: Apollo Camera, L.L.C., Estill Springs, TN (US)

( * ) Notice: Subject to any disclaimer, the term of this patent is extended or adjusted under 35 U.S.C. 154(b) by 377 days.

(21) Appl. No.: 12/802,032

(22) Filed: May 28, 2010
(Under 37 CFR 1.47)

(65) Prior Publication Data

US 2010/0268178 A1    Oct. 21, 2010

Related U.S. Application Data (60) Continuation of application No. 11/430,431, filed on May 9, 2006, now abandoned, which is a division of application No. 10/680,973, filed on Oct. 7, 2003, now Pat. No. 7,041,055.

(60) Provisional application No. 60/416,665, filed on Oct. 7, 2002, provisional application No. 60/424,752, filed on Nov. 8, 2002, provisional application No. 60/424,754, filed on Nov. 8, 2002, provisional application No. 60/424,755, filed on Nov. 8, 2002, provisional application No. 60/425,506, filed on Nov. 12, 2002, provisional application No. 60/425,522, filed on Nov. 12, 2002, provisional application No. 60/425,523, filed on Nov. 12, 2002, provisional application No. 60/439,759, filed on Jan. 13, 2003.

(51) Int. Cl.
*H02J 7/00* (2006.01)

(52) U.S. Cl.
USPC .......................................................... 320/135

(58) Field of Classification Search
None
See application file for complete search history.

(56) References Cited

U.S. PATENT DOCUMENTS

| | | | | |
|---|---|---|---|---|
| 3,603,861 | A | * | 9/1971 | Staats et al. ................... 320/133 |
| 4,593,409 | A | | 6/1986 | Miller |
| 4,734,896 | A | | 3/1988 | Soma et al. |
| 4,746,852 | A | | 5/1988 | Martin |
| 4,849,682 | A | | 7/1989 | Bauer et al. |
| 4,965,738 | A | | 10/1990 | Bauer et al. |
| 5,021,779 | A | | 6/1991 | Bisak |
| 5,119,009 | A | * | 6/1992 | McCaleb et al. .............. 320/127 |
| 5,184,059 | A | | 2/1993 | Patino et al. |
| 5,200,686 | A | | 4/1993 | Lee |
| 5,206,097 | A | | 4/1993 | Burns et al. |
| 5,237,257 | A | | 8/1993 | Johnson et al. |
| 5,399,446 | A | | 3/1995 | Takahashi |
| 5,442,794 | A | * | 8/1995 | Wisor et al. ................... 713/340 |
| 5,479,084 | A | * | 12/1995 | Satsuma et al. ............... 320/136 |
| 5,651,821 | A | * | 7/1997 | Uchida ........................ 118/200 |
| 5,717,306 | A | | 2/1998 | Shipp |

OTHER PUBLICATIONS

"Automatic Battery Discharge Using Real Time Clock," IBM Technical Disclosure Bulletin, Apr. 1994, Col. 37 Issue 4A pp. 189-192.*

* cited by examiner

*Primary Examiner* — Drew A Dunn
*Assistant Examiner* — Robert Grant
(74) *Attorney, Agent, or Firm* — Martin & Ferraro, LLP (57) ABSTRACT

An apparatus and method for rendering a battery safe for disposal by completing a circuit between positive and negative terminals to rapidly deplete the battery of power.

14 Claims, 6 Drawing Sheets

DEVICE AND METHOD FOR RENDERING A BATTERY SAFE FOR DISPOSAL

RELATED APPLICATIONS

This application is a continuation of U.S. application Ser. No. 11/430,431, filed May 9, 2006, now abandoned; which is a divisional of U.S. application Ser. No. 10/680,973, filed Oct. 7, 2003 now U.S. Pat. No. 7,041,055; which claims the benefit of U.S. Provisional Application No. 60/416,665, filed Oct. 7, 2002; U.S. Provisional Application Nos. 60/424,752; 60/424,754; and 60/424,755, each filed Nov. 8, 2002; U.S. provisional Application Nos. 60/425,506; 60/425,522; and 60/425,523, each filed Nov. 12, 2002; and U.S. Provisional Application No. 60/439,759, filed Jan. 13, 2003; all of which are incorporated by reference herein.

BACKGROUND OF THE INVENTION

The present invention relates generally to systems and methods for rendering batteries safe for disposal after use. More specifically, the present invention pertains to battery packs with integrated devices for detecting when the battery is ready for disposal and rendering the battery safe for non-hazardous type disposal. The increased use of batteries in portable and mobile devices, such as cellular telephones and those devices commonly found in hospital environments have created environmental problems owing to the disposal of the spent batteries. For example, many hospitals contract with environmental companies to periodically collect spent batteries from the hospital and dispose of them in an environmentally acceptable fashion. This process is expensive, time-consuming, and not always effective in that a number of batteries end up in standard garbage disposal containers, the contents of which are often incinerated and otherwise disposed by methods that are not always safe. Also, the incineration of such batteries is often hazardous because of the chemical composition of the battery. For example, lithium is a commonly used material in batteries. Lithium reacts quite violently to water, sometimes causing explosions. Such batteries can also emit harmful gases upon partial destruction. What is needed then is a device that renders a battery inert after the usage of the battery is complete. Once in an inert state, the battery may then be treated as standard waste material and incinerated or buried in landfills without concern about environmental safety.

In U.S. Pat. No. 5,717,306 (the "'306 patent") issued to Shipp, a battery identification and power interrupt system is described. In one embodiment, the '306 patent describes a battery pack that is equipped with a preprogrammed identification device that can communicate with a microprocessor built into the device. Preferably, the battery powers the microprocessor for the purpose of interrogating the battery to ensure that the appropriate battery is used in the device. This is accomplished through a third terminal on the battery that acts as a data terminal to pass information bi-directionally from the battery to the processor and vice-versa. Though not needed to understand the present invention, portions of the '306 patent (incorporated by reference in U.S. Provisional Application No. 60/425,506, of which this application claims the benefit of) are included in the present specification for background information only. In particular, the embodiment of FIGS. 1 to 6 of the present application generally corresponds to the embodiment described and shown in FIGS. 1 to 6 of the '306 patent. The present invention includes an improvement over the '306 patent in that it adds the capability of rendering a battery inert using a third terminal of the battery, for example, a data terminal.

SUMMARY OF THE INVENTION

In one preferred embodiment, the present invention includes an apparatus for rendering a battery safe for disposal. The apparatus includes a positive contact adapted to touch a positive terminal of the battery; a negative contact adapted to touch a negative terminal of the battery; and a controller operatively connected to said positive and negative contacts to close a circuit between the positive and negative terminals of the battery, said controller being configured to rapidly deplete the battery of power upon an occurrence of a pre-programmed event.

In another preferred embodiment, the present invention includes a method for rendering a battery safe for disposal. The method includes powering a device with a battery having a positive terminal and a negative terminal; determining when the device is no longer actively being used by a person; and completing a circuit between the positive terminal and the negative terminal of the battery to rapidly deplete the battery of power.

In a further preferred embodiment, the present invention includes a method for rendering a battery safe for disposal. The method includes expending an amount of power from a battery having a positive terminal and a negative terminal to power a device; reducing the power expended; moving a discharge arm having a positive contact and a negative contact over the respective positive and negative terminals of the battery; and completing a circuit between the positive and negative terminals of the battery to rapidly deplete the battery of power.

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

DESCRIPTION OF THE PREFERRED EMBODIMENT

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

Figure 1:
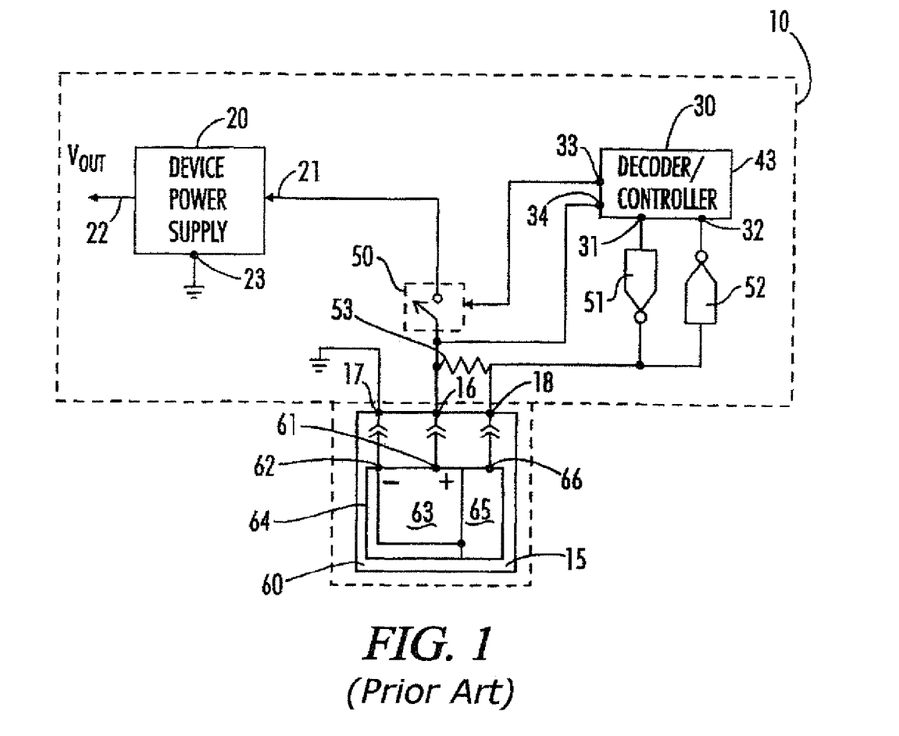
FIG. 1 is an electrical schematic and block diagram of a battery identification and power interrupt system.

Looking first at FIG. 1, the general arrangement of the battery identification and power interrupt system is shown. A battery powered device 10 is the host for the components of the system. Device 10 can include a variety of functional circuits and devices which are not shown. Device 10 includes a conventional device power supply 20 which typically will convert the electrical voltage supplied by a battery at battery power input terminal 21 to the operational voltage or voltages required by device 10 and provide that converted voltage as $V_{OUT}$ at device power supply output terminal 22. Device power supply 20 will usually further include appropriate voltage regulators and filtering circuits, as needed by the performance characteristics of device 10.

Also, electrically and mechanically a part of device 10 is a battery housing 15 which can be formed in a wide variety of sizes and shapes as necessary to conform to the size and shape of battery or battery packs to be retained in housing 15.

The other elements of device 10 are decoder/control unit 30 and power interrupt switch 50. Decoder unit 30 provides the means for receiving and decoding battery identification data, for making the data and code comparisons necessary to insure battery compatibility, and for sending appropriate power interrupt signals to power interrupt switch 50, as will be described in more detail below.

Conventional positive and negative electrical contacts 16 and 17 are attached to battery housing 15 for purposes of making mechanical and electrical contact with corresponding positive and negative terminals 61 and 62 on a removable battery pack 60.

Positive and negative terminals 61 and 62 are physically attached to enclosure 64 of battery pack 60 and further make electrical connection to one or more battery cells 63 internal to battery pack 60. Battery pack 60 further includes an integral battery encoder 65, which provides the means in battery pack 60 for the electrical storage of battery identification data, and for communicating that battery identification data externally through a data terminal 66 attached to battery pack enclosure 64. Accordingly, battery housing 15 further includes a data contact 18 which makes mechanical and electrical contact with battery pack data terminal 66 when the battery pack 60 is installed.

As further seen in FIG. 1, additional interface circuitry is provided within device 10 to insure proper functioning of the system as described below. Thus, negative terminal 62 of battery pack 60 will be electrically grounded to the ground side of device 10 through negative contact 17. Positive terminal 61 of battery pack 66 will be electrically connected to power interrupt switch 50 so that the flow of current to be supplied by battery pack 60 to device 10 can be enable or disabled in accordance with the functioning of power interrupt switch 50, Decoder 30 can receive its operational power directly from battery pack 60 through decoder power input 34 as shown on FIG. 1. Alternatively, decoder 30 can be provided with independent internal or external power. The communications between encoder unit 65 and decoder 30 are facilitated by electrical connection between battery housing data contact 18 and data output 31 and input 32 terminals of decoder 30 through data transmit line gate 51 and receive line gate 52. A pull-up resistor 53 electrically connects battery encoder 66 to the primary battery power line of device 10.

Although data terminal 66 and data contact 18 are shown as separate from their corresponding power terminals and contacts, it would be possible to combine the data terminal and contacts with a power terminal and superimpose the battery identification signals.

The battery encoder 65 portion of battery pack 60 can be a Model DS2400 Silicon Serial Number integrated circuit manufactured by Dallas Semiconductor. In such an embodiment, all data communication to and from encoder 65 is accomplished by a single interface line, as shown on FIG. 1. Battery identification data stored in encoder 65 can then include an eight-bit digitally encoded model or type number and a forty-eight bit battery identification code. Encoder 65 in this embodiment can further include an eight-bit check value which can be used, as described below, to confirm that battery identification data from encoder 65 has been correctly received by the system.

The data stored in encoder 65 is accessed during read and write time slots, as shown on FIGS. 2a, 2b, 3a, and 3b, with power for encoder 65 being derived from high logic level pulses at the beginning of a write or read time slot.

Figure 6:
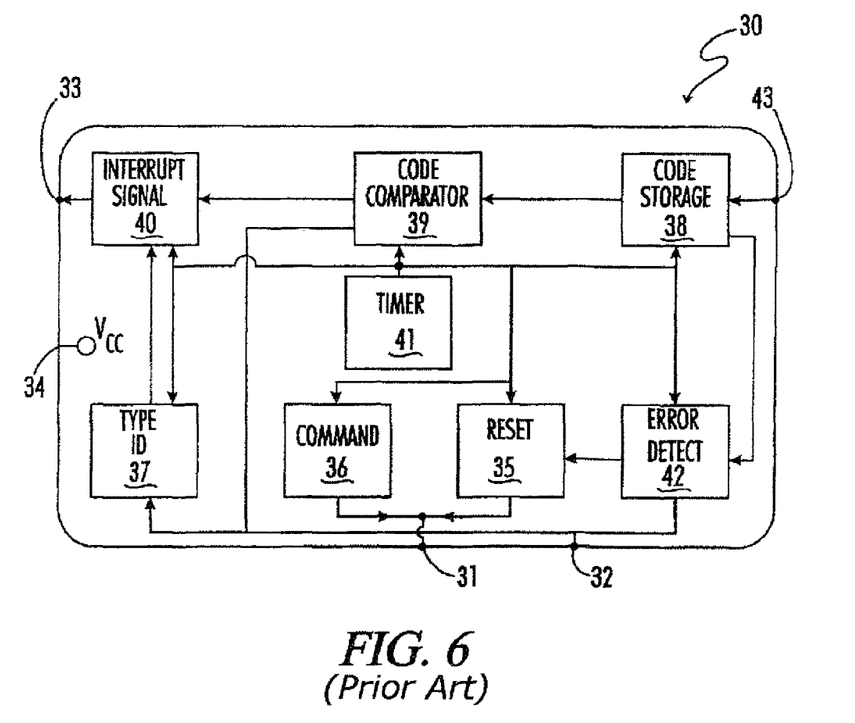
FIG. 6 is a block diagram representation of the decoder/controller unit of the system.

To fully implement all the features available from encoder 65 of battery pack 60 as described above, a decoder/control 30 having functional modules which correspond to encoder 65 of the preferred embodiment is illustrated in more detail in FIG. 6. A timer circuit 41, which can be implemented in the form of a conventional programmable microprocessor, provides the various timing and logic signals in a conventional manner to other functional modules of decoder 30. These other modules can be physically separate from timer 41 or integral to it.

Figure 5:
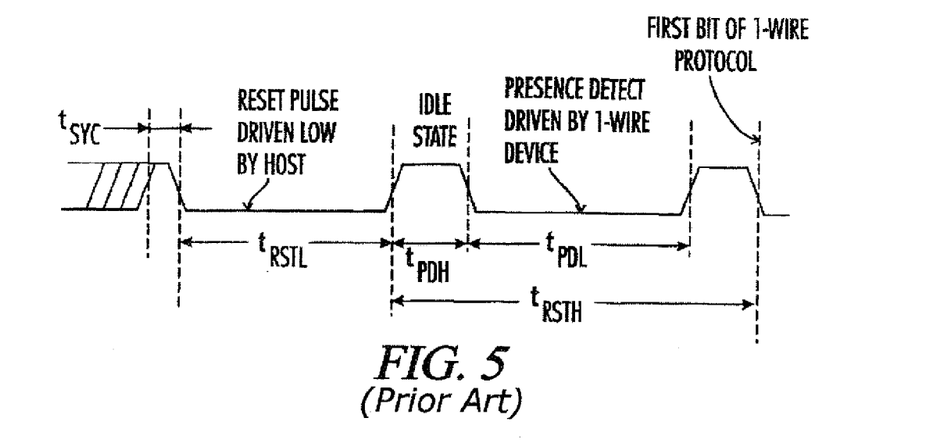
FIG. 5 represents the sequence and logic levels during generation of a reset pulse signal by the device decoder and generation of presence detect signal by the battery pack encoder.

A reset pulse generator 35 is used to provide a battery pack control signal in the form of reset pulses to encoder 65 of battery pack 60, as shown on FIG. 5. This allows encoder 65 to progress in an organized sequence from an initial reset condition to a condition where it can receive control signals from decoder 30 and then communicate battery identification data, including the type number, the battery identification code, and the check value, such states of encoder 65 being illustrated on FIG. 4. A command word generator 36 is also included in decoder 30 to generate other necessary control signals from the system to encoder 65.

A type number decoder/comparator module 37 receives the type number from encoder 65 and makes the necessary comparisons to a pre-programmed type number stored in module 37, which in the preferred embodiment is the hexadecimal number 01. Battery identification code comparator module 39, also part of decoder 30, receives the battery identification code from encoder 65 and makes a comparison of the battery identification code to a device identification code stored in device code memory module 38. Code comparator module 39 also provides a comparison signal to interrupt signal generator 40 to indicate whether there has been a proper match of the battery identification code with the device identification code. If the comparison signal from code comparator module 39 indicates a code mismatch, interrupt signal generator 40 then sends a power interrupt signal to interrupt switch 50. This causes interrupt switch 50 to open, thereby disabling electrical connection of device power supply 20 to battery pack 60.

Optionally, a device identification code input port 43 is provided on decoder 30 whereby a new or changed device identification code can be downloaded to code memory module 38. Finally, an error detection module 42 is optionally provided in a preferred embodiment. Error detection module 42 provides the means for generating an error detection signal, receiving the check value signal from encoder 65, and for making the appropriate comparison to confirm whether the data from encoder 65 has been received correctly by encoder 30.

Having described the basic functional components and modules of the system, the electrical operation of the system can now be understood. When a battery pack 60 is initially installed within battery housing 15 of device 10 and mechanical and electrical connection is made between positive, negative, and data terminals 61, 62, and 66 of battery pack 60 and positive, negative, and data contacts 16, 17, and 18 of battery housing 15, decoder/control unit 30 is powered up. A reset pulse is then generated by reset pulse generator 35 of decoder 30 and sent to encoder 65 of battery pack 60, placing the encoder in the first or reset state shown on FIG. 4. Encoder 65 then generates a presence detect signal, as shown on FIG. 5, so that decoder 30 can determine that the battery pack 60 and encoder 65 have been electrically connected. Encoder 65 then assumes the second state shown on FIG. 4.

Figure 2A:
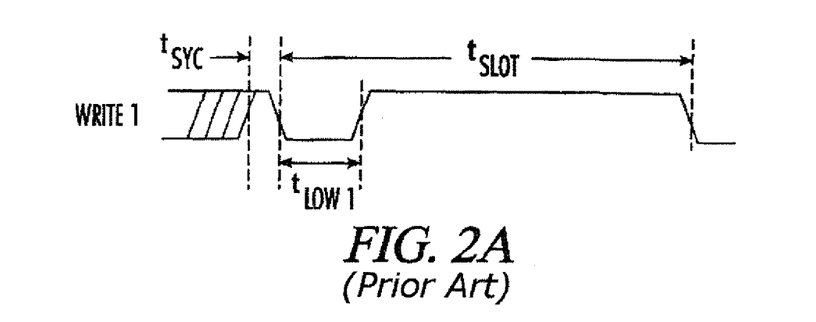
FIGS. 2a and 2b are graphical representations of the signal levels and signal timing associated with the communication of control signals from the system decoder to the battery pack encoder in a preferred embodiment of the system, where $t_{syc}$ represents the synchronization signal, $t_{low1}$ represents the low logic signal for a write 1 time slot, $t_{low0}$ represents the low logic signal for a write 0 time slot, and $t_{slot}$ represents the duration of a single write time slot.
Figure 2B:
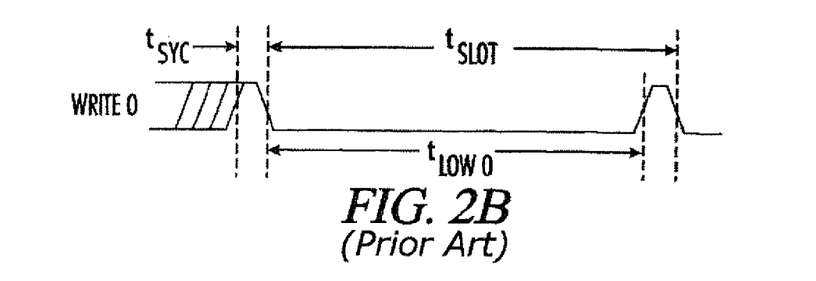
Figure 3A:
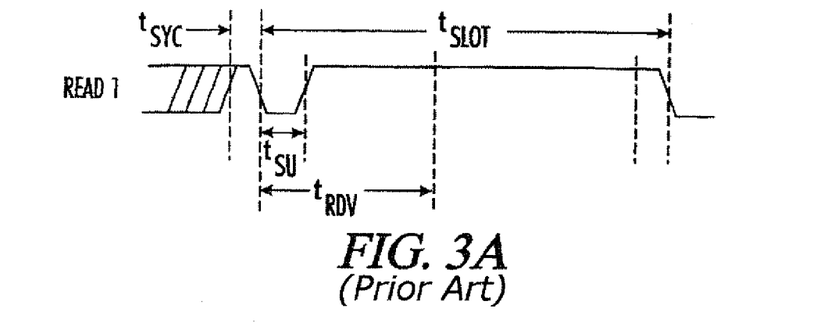
FIGS. 3a and 3b are graphical representations of the signal levels and signal timing associated with communication of battery identification data from the battery pack encoder to the system decoder, where $t_{syc}$ represents the synchronization signal, $T_{SU}$ represents the read data setup signal, $t_{RDV}$ represents the read data valid signal, and $t_{slot}$ represents the duration of a single read time slot.
Figure 3B:
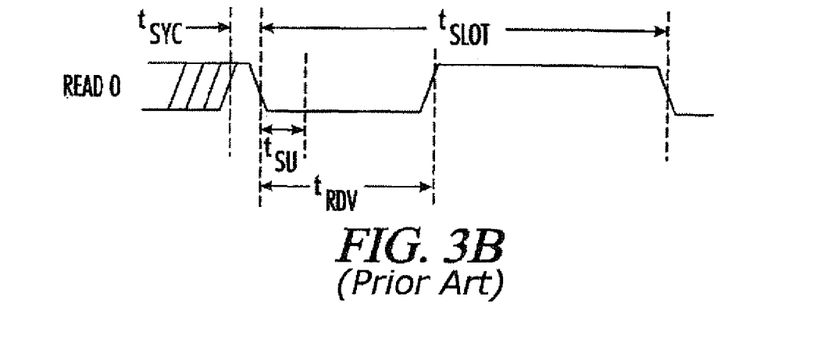
Figure 4:
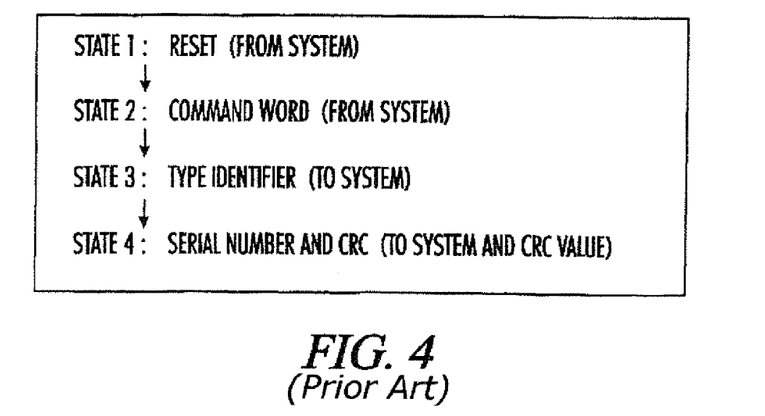
FIG. 4 is a table showing the sequence of states which are assumed by the battery encoder used in a preferred embodiment of the system.

Next, command word generator 36 of decoder 30 transmits a command word battery pack control signal to encoder 65, consisting of eight write time slots as illustrated in FIGS. 2a and 2b. In a preferred embodiment, the command word for encoder 65 is the hexadecimal number 0F. Upon receipt of the proper command word, encoder 65 assumes the third state as shown on FIG. 4. Accordingly, encoder 65 generates the first portion of the battery identification data, consisting of the type number, in eight read time slots as shown on FIGS. 3a and 3b. Type number decoder/comparator module 37 of decoder 30 compares the transmitted type number to its internally stored number and, if a match is confirmed, causes decoder 30 to issue forty-eight read time slot control signals to encoder 65. This causes encoder 65 to transmit the forty-eight bit battery identification code to code comparator module 39 of decoder 30. Where error detection is required, encoder 65 will then transmit a preprogrammed eight bit error check value, which has been calculated based on the type number and the battery identification code. To read this value, error detection module 42 of decoder 30 must issue eight read time slots. Error detection module 42 internally generates an error detection code by making a calculation based on all of the bytes of information that have been passed to decoder 30 from encoder 65.

Upon confirmation that the transmission of battery identification data from encoder 65 has been error free, code comparator module 39 of decoder 30 makes a digital comparison between the received battery identification code and the device identification code which has been retrieved from code memory module 38. If a match is confirmed, code comparator module 39 generates a signal for interrupt signal generator 40. A power interrupt signal then is available at power interrupt signal port 33 for electrical communication to power interrupt switch 50. Power interrupt switch 50 then closes, allowing the delivery of electrical power from battery pack 60 to device power supply 20.

It will also be apparent from FIG. 6 that if a mismatch regarding the type number is determined by type number module 37, a mismatch signal can be transmitted to interrupt signal generator 40, causing power interrupt switch 50 to open.

Figure 7:
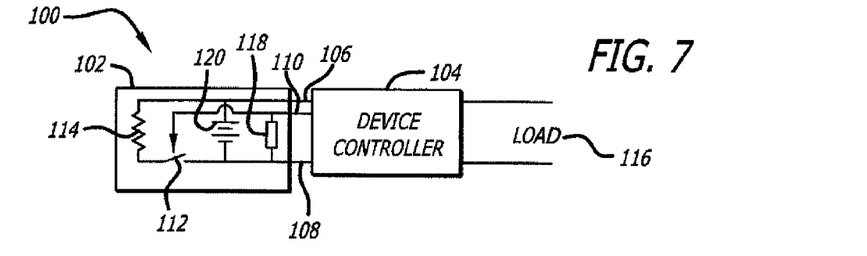
FIG. 7 is a block diagram of a battery discharge system according to one preferred embodiment of the present invention.

FIG. 7 is a schematic diagram of a battery pack generally designated 102 as part of the overall battery discharge system generally designated 100. Battery pack 102 is connected to device controller 104 through three terminals. The positive terminal of the battery, 106, is connected to the device controller, as is the negative terminal 108. In addition, a data terminal 110 is connected to the device controller. Data terminal 110 is connected to a battery identification circuit as described above in relation to FIGS. 1 to 6 and in U.S. Pat. No. 5,717,306, incorporated herein by reference. Relay 112 is connected in series with the resistor 114 between the positive terminal 106 and the negative terminal 108, Data terminal 110 is the actuator for the relay 112. Device controller 104 is connected to a load 116. Relay 112 can be either mechanical type or electrical type, both of which are well known in the art.

Figure 8A:
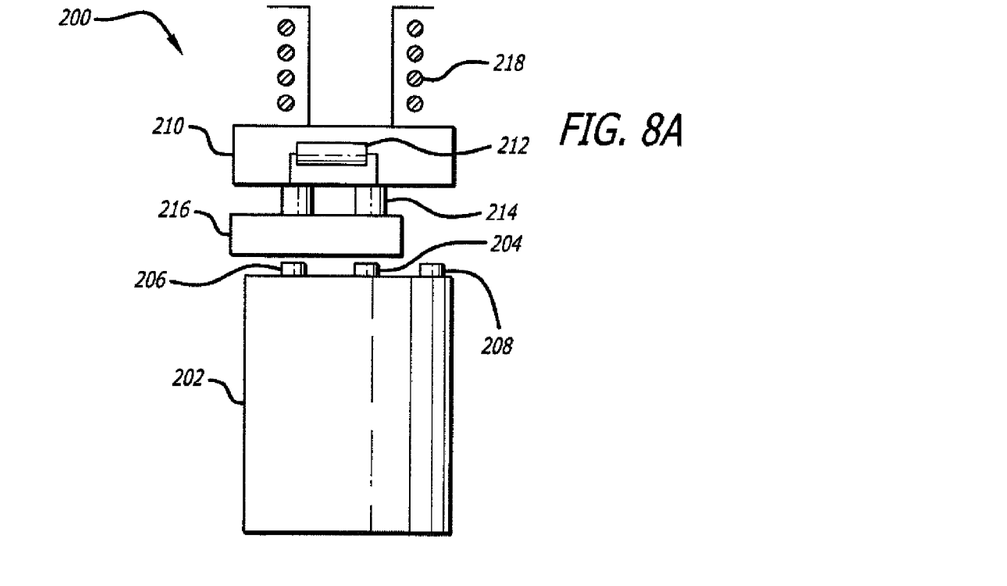
FIG. 8A is a side elevational view of a battery discharge system according to another preferred embodiment of the present invention with a safety lock in an engaged position.
Figure 8B:
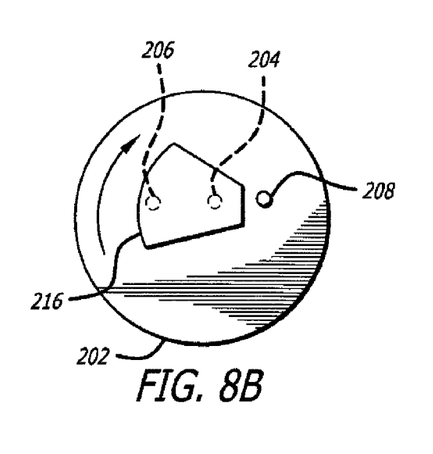
FIG. 8B is a top view of the system of FIG. 8A.
Figure 8C:
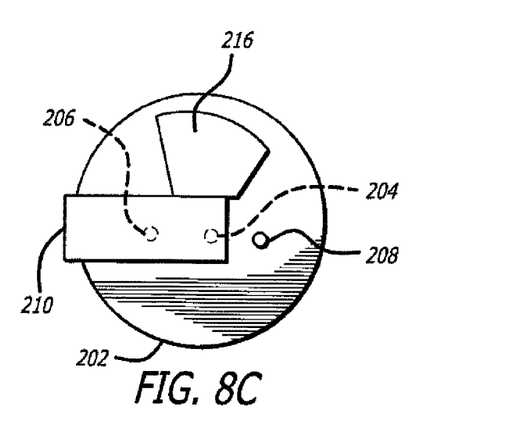
FIG. 8C is a top view of the system of FIG. 8A with the safety lock in a discharged position.

Now turning to FIG. 8A, a second embodiment of the present invention generally designated as 200, the battery 202 is depicted with three terminals 206, 204, and 208; terminal 204 being the positive output of the battery, 206 the negative, and 208 the data terminal. Discharge arm 210 comprises a discharge resistor 212 and discharge electrodes 214. Discharge arm 210 is biased against safety lock 216; this is a position prior to the battery having been inserted into the instrument. FIG. 8B of this embodiment shows the safety lock plate 216 in a position covering the positive and negative terminals 206 and 204, so that discharge electrodes 214 are not in contact with the positive and negative terminals 206 and 204. The battery is used in this position, that is, terminals 206, 204, and 208 are in contact with the input terminals to the device to be powered (not shown here) while the battery is thus in use. Discharge electrodes 214 and discharge resistance 212 is not in contact with terminals 206 and 204 of the battery. Upon completion of the use of the battery, the battery is removed by rotation, for example, a bayonet lock. Upon rotation, safety lock 216 is rotated so that it no longer makes contact with discharge electrodes 214 as shown in FIG. 8C. Spring bias 218 thus forces the discharge mechanism 210 down so that the discharge electrodes 214 make electrical contact with terminals 206 and 204 of the battery.

Turning again to FIG. 7, this embodiment functions as follows: device controller 104 contains appropriate memory and circuitry for storing software or firmware programs. This device controller 104 operates the supplies power to the load and operates the device, for example, setting and selecting waveforms, rotational speed, duty cycle, or other such parameters. In addition, the program contained in device controller 104 performs the function of battery recognition such as described above in relation to FIGS. 1 to 6 and in the '306 patent through component 118 contained in the battery pack. An example of how this preferred embodiment works is the use of such a system to power, for example, a small bone drill in medical applications. After the procedure is completed, device controller 104 signals the relay 112 to close via data terminal 110. Relay 112 is a normally open relay that closes upon a pulse being transmitted to the actuator of the relay via terminal 110 and remains closed permanently. Upon closure of relay 112, the battery 120 is discharged through resistance 114 until substantially all of the chemistry in the battery is used up and zero volts appear at the terminal. The program contained in device controller 104 decides when to signal relay 112 for closure via a preprogrammed decision-making loop that can be, for example, lack of activity for a certain period of time. In the example of the load being a small bone drill, if, for example, the drill was not used for a period of 30 minutes, the software located in device controller 104 would then signal the relay 112 through data terminal 110 to permanently close. This would result in the discharge of the battery which would in effect use the chemistry that was still available in the otherwise partially discharged battery. The U.S. Environmental Protection Agency has ruled that a lithium sulfur dioxide battery is non-hazardous if fully discharged to deplete the reactive components to a low level.

Turning now to FIGS. 8A to 8C, the mechanical discharge mechanism 210 is put in place to discharge the battery 202 upon removal of the battery from the system. A bayonet lock for the battery pack, for example, requiring rotational movement of the battery pack to remove the battery pack from the instrument allows safety lock 216 to be rotated (FIG. 8B) such that discharge mechanism 210 drops down (FIG. 8C) and the discharge electrodes 214 place resistance 212 electrically across the active terminals 206 and 204 of the battery. Thus, upon removal of the battery from the device, the battery starts its discharge through resistance 212. Once the terminal voltage reaches zero or near zero, the active ingredient is consumed, for example, in the lithium sulfur dioxide battery, so that the battery becomes non-hazardous.

Figure 9:
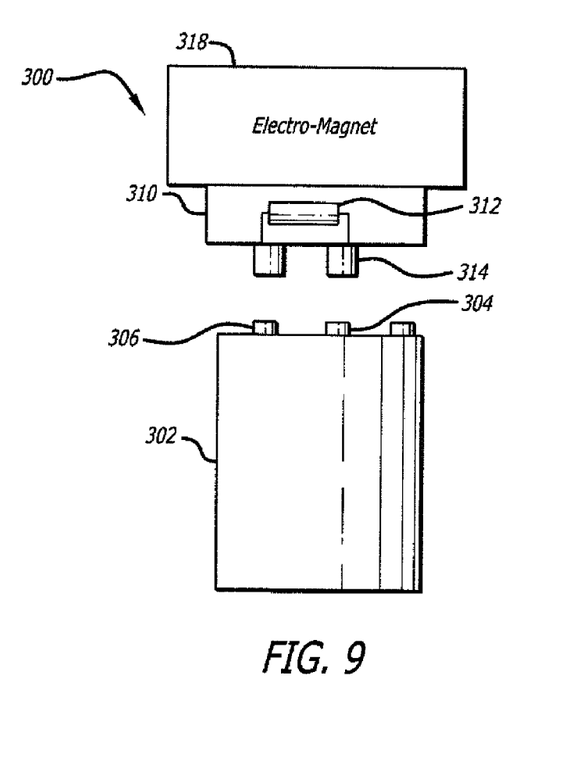
FIG. 9 is a side elevational view of a battery discharge system according to another preferred embodiment of the present invention.

FIG. 9 shows another preferred embodiment of an apparatus 300 for rendering a battery 302 safe for disposal. Apparatus 300 includes a discharge arm 310 having a resistance 312 and positive contact adapted to touch a positive terminal 306 of battery 302 and a negative contact adapted to touch a negative terminal 304 of battery 302. Discharge arm 310 is moveable between an engaged position where the positive and negative contacts touch the respective positive and negative terminals 306, 306 of battery 302 to complete a circuit and rapidly deplete battery 302 of power and a disengaged position where the positive and negative contacts are separated from the respective positive and negative terminals 306, 304 of battery 302. Discharge arm 310 is adapted to move to the engaged position when a device being powered by battery 302 is turned off. Discharge arm 310 is restrained in the disengaged position by an electro-magnet 318 powered by battery 302. Electro-magnet 318 is turned off when the device being powered by battery 302 is turned off.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for rendering a battery safe for disposal, said apparatus comprising:
a positive contact adapted to touch a positive terminal of the battery;
a negative contact adapted to touch a negative terminal of the battery; and
a controller operatively connected to said positive and negative contacts to close a circuit between the positive and negative terminals of the battery, said controller being configured to rapidly deplete the battery of power upon an occurrence of a pre-programmed event, said controller being adapted to track the number of times the battery is used and close said circuit after a pre-set number of uses.

2. The apparatus of claim 1, wherein said controller is adapted to time the usage of the battery and close said circuit after a pre-selected amount of time has elapsed.

3. The apparatus of claim 1, wherein said controller is adapted to estimate the amount of battery life remaining after a use of the battery and close said circuit when the amount of battery life remaining is less than a pre-determined threshold.

4. The apparatus of claim 1, wherein said controller is adapted to indicate the availability of battery power for a given function.

5. An apparatus for rendering a battery safe for disposal, said apparatus comprising:
a discharge arm having a positive contact adapted to touch a positive terminal of the battery and a negative contact adapted to touch a negative terminal of the battery; said discharge arm being moveable between an engaged position where said positive and negative contacts touch the respective positive and negative terminals of the battery to complete a circuit and rapidly deplete the battery of power and a disengaged position where said positive and negative contacts are separated from the respective positive and negative terminals of the battery, said discharge arm being adapted to move to the engaged position when a device being powered by the battery is turned off, said discharge arm being restrained in the disengaged position by an electro-magnet powered by the battery, said electro-magnet being turned off when the device being powered by the battery is turned off.

6. The apparatus of claim 5, wherein said discharge arm is biased to the engaged position.

7. The apparatus of claim 6, further comprising a blocking plate adapted to at least partially cover the positive and negative terminals of the battery to separate said discharge arm from the terminals of the battery when said discharge arm is in the disengaged position.

8. The apparatus of claim 7, wherein said blocking plate is rotatably moveable to uncover the positive and negative terminals of the battery and permit said discharge arm to move to the engaged position.

9. The apparatus of claim 6, further comprising a spring for biasing said discharge arm to the engaged position.

10. The apparatus of claim 5, wherein the battery has a longitudinal axis and said discharge arm is adapted to move to the engaged position when the battery is rotated about its longitudinal axis.

11. A method for rendering a battery safe for disposal, the method:
powering a device with a battery having a positive terminal and a negative terminal;
determining when the device is no longer actively being used by a person;
determining whether enough battery power remains for another active use by a user; and
completing a circuit between the positive terminal and the negative terminal of the battery to rapidly deplete the battery of power after it is determined that not enough battery power remains for another active use by a user.

12. The method of claim 11, further comprising tracking the amount of time elapsed since the device was actively used.

13. The method of claim 12, wherein the completion of the circuit occurs after a pre-programmed amount of time has elapsed since the device was actively used.

14. A method for rendering a battery safe for disposal, the method comprising:

expending an amount of power from a battery having a positive terminal and a negative terminal to power a device and to power an electro-magnet adapted to restrain a discharge arm in a disengaged position; and     turning off the device and the electro-magnet to move the discharge arm from the disengaged position to an engaged position where a positive contact and a negative contact of the discharge arm engage the respective positive and negative terminals of the battery to complete a circuit between the positive and negative terminals of the battery to rapidly deplete the battery of power.

\* \* \* \* \*